(12) United States Patent
Chang

(10) Patent No.: US 7,811,137 B2
(45) Date of Patent: Oct. 12, 2010

(54) NETWORK SOCKET CONNECTOR WITH BUILT-IN IP BOX FUNCTION

(76) Inventor: Nai-Chien Chang, 5F., No.15, Lane 117, Sec. 4, Sanhe Rd., Sanchong City, Taipei County 241 (TW)

( * ) Notice: Subject to any disclaimer, the term of this patent is extended or adjusted under 35 U.S.C. 154(b) by 0 days.

(21) Appl. No.: 12/637,062

(22) Filed: Dec. 14, 2009

(65) Prior Publication Data

US 2010/0203769 A1 Aug. 12, 2010

(30) Foreign Application Priority Data

Feb. 12, 2009 (TW) .............................. 98202025 U

(51) Int. Cl.
*H01R 24/00* (2006.01)
(52) U.S. Cl. ..................................................... 439/676
(58) Field of Classification Search ................ 439/676, 439/541.5, 490, 540.1
See application file for complete search history.

(56) References Cited

U.S. PATENT DOCUMENTS

| | | | | |
|---|---|---|---|---|
| 6,540,551 B1 * | 4/2003 | Wang | ....................... | 439/541.5 |
| 6,758,699 B1 * | 7/2004 | Hwang et al. | ............... | 439/676 |
| 7,121,898 B2 * | 10/2006 | Murr et al. | .................. | 439/676 |
| 2005/0282441 A1 * | 12/2005 | Murr et al. | .................. | 439/676 |

* cited by examiner

*Primary Examiner*—Chandrika Prasad
(74) *Attorney, Agent, or Firm*—Chun-Ming Shih; HDLS IPR Services

(57) ABSTRACT

A network socket connector with built-in IP BOX function includes a base, a front cover, a circuit board, an upper cover and a metallic housing. A rear surface of the base is provided with a plurality of conductive pins and a front surface thereof is provided with a plurality of electrode terminals. The front cover is assembled to the front end of the base and has a connecting port. The circuit board has a network AV streaming broadcast circuit. The upper cover is assembled with the base and the front cover. The metallic housing is configured as a hollow body for sealing the base, the front cover, the circuit board and the upper cover. When a plug of a network line is inserted into the connecting port to be electrically connected with the electrode terminals, the Internet can be accessed by the network AV streaming broadcast circuit of the circuit board.

8 Claims, 4 Drawing Sheets

NETWORK SOCKET CONNECTOR WITH BUILT-IN IP BOX FUNCTION

BACKGROUND OF THE INVENTION

1. Field of the Invention

The present invention relates to a connector, and in particular to a network socket connector capable of accessing the Internet directly.

2. Description of Prior Art

Recently, the input/output panel of a computer host has a network socket connector for electrically connecting to a network card that is inserted to a main board of the computer. When a user inserts a RJ-45 type plug of a network line into the network socket connector together with a modem, the Internet can be accessed. Thus, the user can browse web pages, transmit or download data, or send e-mails to a remote person.

Some network cards are vertically inserted into the main board of the computer, and however, such a vertical insertion of the network card may often block the thermal convection between the heat generated by the components on the main board and the air outside of the computer casing. Thus, it is necessary to mount a fan on a front, rear or side surface of the computer casing so as to dissipate the heat inside the computer casing.

With the advancement of science and technology, the network card has been integrated into the main board of the computer, whereby more space in the computer casing can be spared for the heat dissipation of other electronic components on the main board. However, such an arrangement increases the difficulty in designing and manufacturing the main board of the computer.

Therefore, it is an important issue for the present Inventor to simplify the design and manufacture of the main board of the computer.

SUMMARY OF THE INVENTION

In order to solve the problems in conventional art, the present invention is configured to integrate a network socket connector and a network AV streaming broadcast box together. With this arrangement, when a plug of a network line is inserted into the network socket connector, the Internet can be accessed immediately. Further, the main board of an electronic device electrically connected to the network socket connector has signal input ports having AV terminals to which various AV output apparatuses can be connected. When the plug of the network line is inserted into the network socket connector and the Internet is accessed by means of the network AV streaming broadcast circuit, another function of receiving remote control can be achieved.

The present invention is to provide a network socket connector with built-in IP BOX function. The network socket connector allows a network line to be inserted therein and includes:

a base with its rear surface having a plurality of conductive pins extending outside the base and its front surface having a plurality of electrode terminals, the plurality of electrode terminals being electrically connected to the plurality of conductive pins by means of electronic components;

a front cover assembled at a front end of the base, the front cover having a connecting port, the interior of the connecting port having a plurality of insertion slots for the insertion of the plurality of electrode terminals;

a circuit board with its one end having a plurality of insertion holes for the insertion of the conductive pins to be electrically connected to the circuit board, a plurality of conductive terminals being provided on the circuit board adjacent to the insertion holes for electrically connecting to a main board, the circuit board having a network AV streaming broadcast circuit;

an upper cover assembled with the base and the front cover; and a metallic housing configured as a hollow body for sealing the base, the front cover, the circuit board and the upper cover.

After a plug of the network line is inserted into the connecting port, the Internet can be accessed directly for transmitting or downloading data by means of the network AV streaming broadcast circuit on the circuit board.

DETAILED DESCRIPTION OF THE INVENTION

The characteristics and technical contents of the present invention will be described with reference to the accompanying drawings. However, the drawings are illustrative only but not used to limit the present invention.

Figure 1:
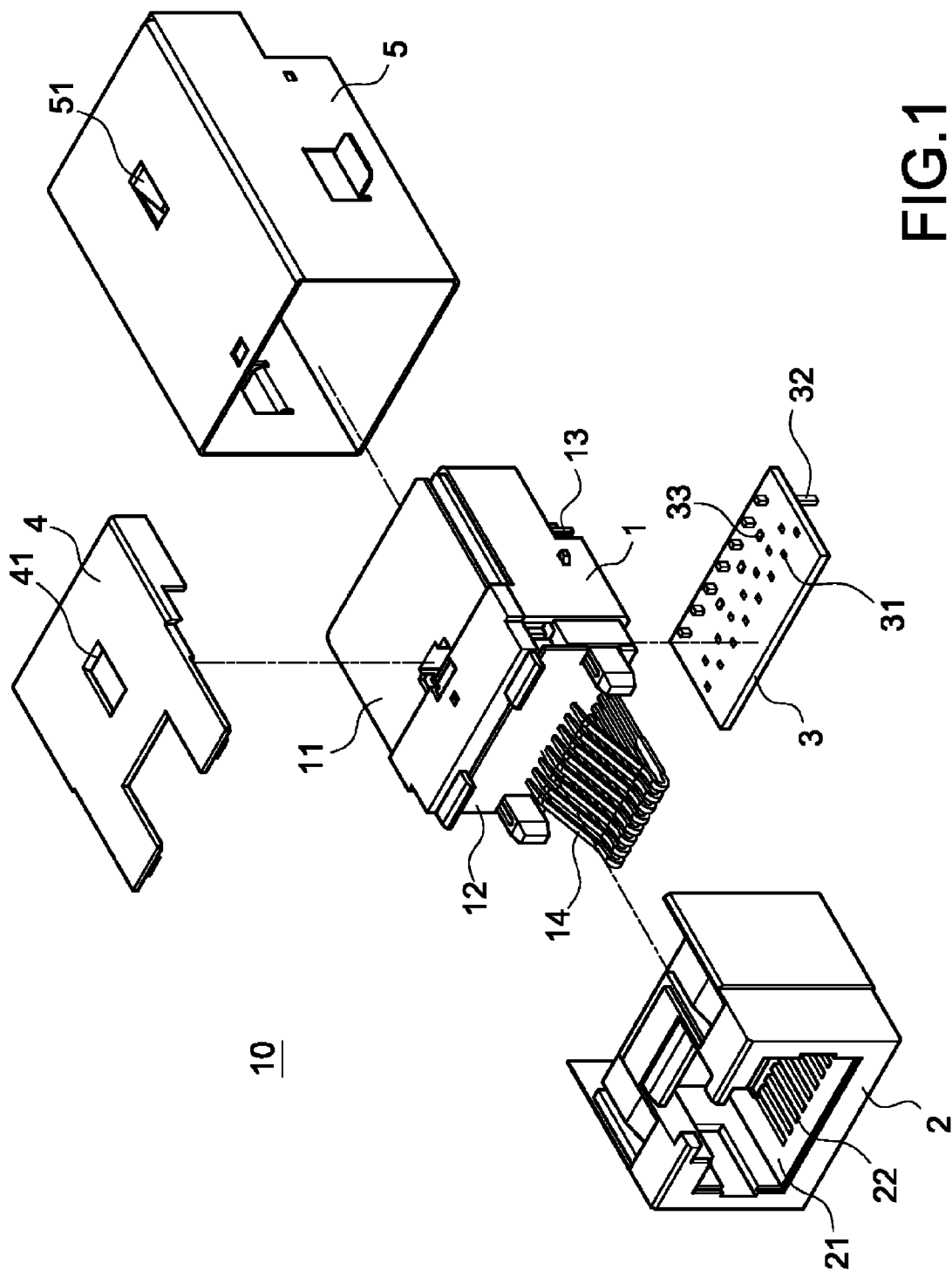
FIG. 1 is an exploded perspective view showing a network socket connector of the present invention.
Figure 2:
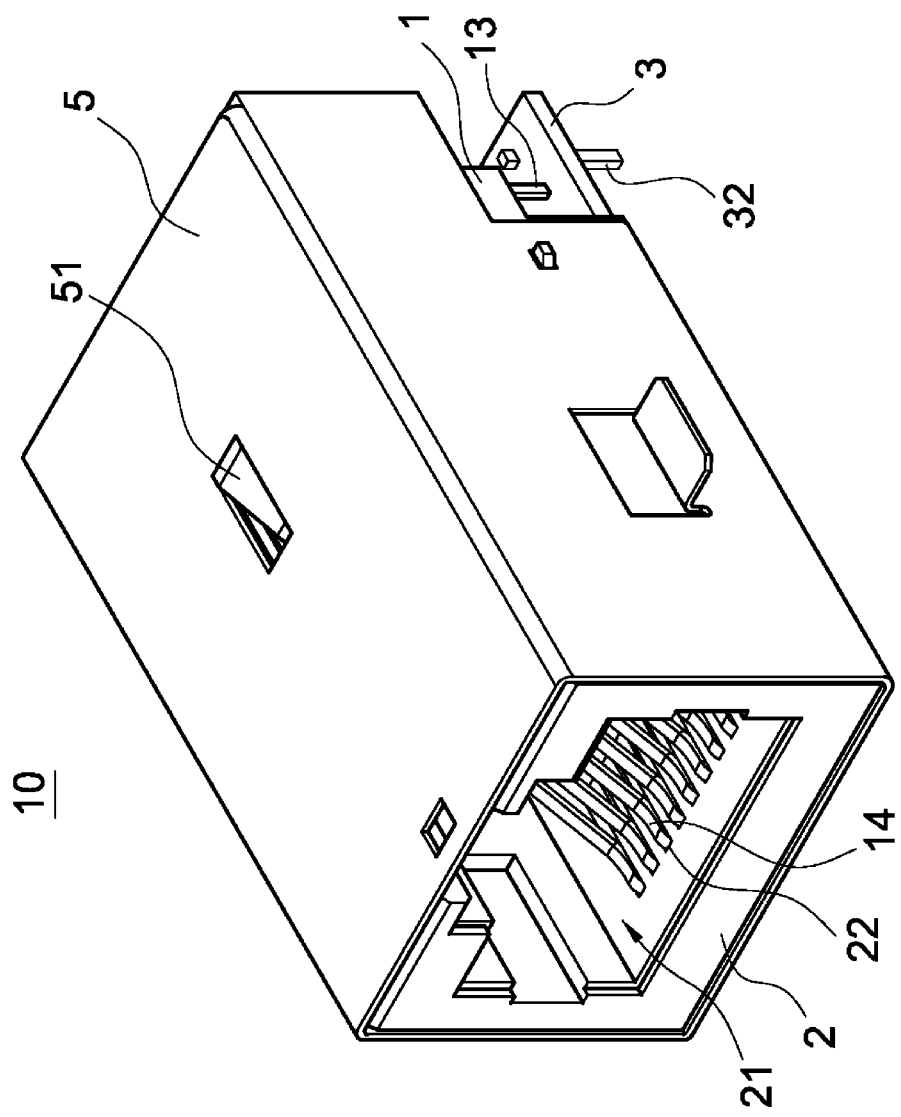
FIG. 2 is a perspective view showing the external appearance of the network socket connector of the present invention.

Please refer to FIGS. 1 and 2. FIG. 1 is an exploded perspective view showing a network socket connector of the present invention, and FIG. 2 is a perspective view showing the external appearance of the network socket connector of the present invention. As shown in these figures, the present invention provides a network socket connector 10 with built-in IP BOX function, which includes a base 1, a front cover 2, a circuit board 3, an upper cover 4 and a metallic housing 5.

The base 1 is configured as a hollow casing. The interior of the base 1 is provided with a filter module (not shown). The filter module is electrically connected to a first adapting circuit board 11 above the base 1 and a second adapting circuit board 12 in front of the base 1. The first adapting circuit board 11 is electrically connected to a plurality of conductive pins 13 extending outside the base 1. Further, the second adapting circuit board 12 is electrically connected to a plurality of electrode terminals 14. The electrical connection between the electrode terminals 14 and the conductive pins 13 is achieved by means of the electronic components including the second adapting circuit 12, the filter module, and the first adapting circuit board 11.

The front cover 2 is assembled to the front end of the base 1. The front cover 2 has a connecting port 21 in which a plurality of insertion slots 22 is provided. When the front cover 2 is assembled at the front end of the base 1, the plurality of electrode terminals 14 is inserted into the insertion slots 22 respectively.

The circuit board 3 has a network AV streaming broadcast circuit 33 in which a device (referred to as an IP BOX) for integrating images, sounds and various network communication protocols is provided. A tuner is provided on the network AV streaming broadcast circuit 33. The tuner is configured to receive and switch channel signals of wireless television net and cable television net. In addition, the user can transmit personal AV signals to others by means of the tuner. One end of the circuit board 3 has a plurality of insertion holes 31 into which the conductive pins 13 are inserted to be electrically connected to the circuit board 3. A plurality of conductive terminals 33 is electrically connected to circuit board 3 adjacent to the insertion holes 31. The conductive terminals 32 are electrically connected to a main board (not shown) of an external electronic device.

The upper cover 4 is assembled with the base 1 and the front cover 2. The top surface of the upper cover 4 has an opening 41. The upper cover 4 is configured to prevent the first adapting circuit board 11 from suffering damage due to foreign objects.

The metallic housing 5 is configured as a hollow body. The top surface of the metallic housing 5 is provided with an elastic piece 51. When the metallic housing 5 is used to seal the base 1, the front cover 2, the circuit board 3 and the upper cover 4, the elastic piece 51 is engaged in the opening 41 of the upper cover 4, thereby preventing against the detachment of the metallic housing 5. Further, the metallic housing 5 is configured to protect against external electromagnetic interference when the network socket connector 10 transmits signals.

Figure 3:
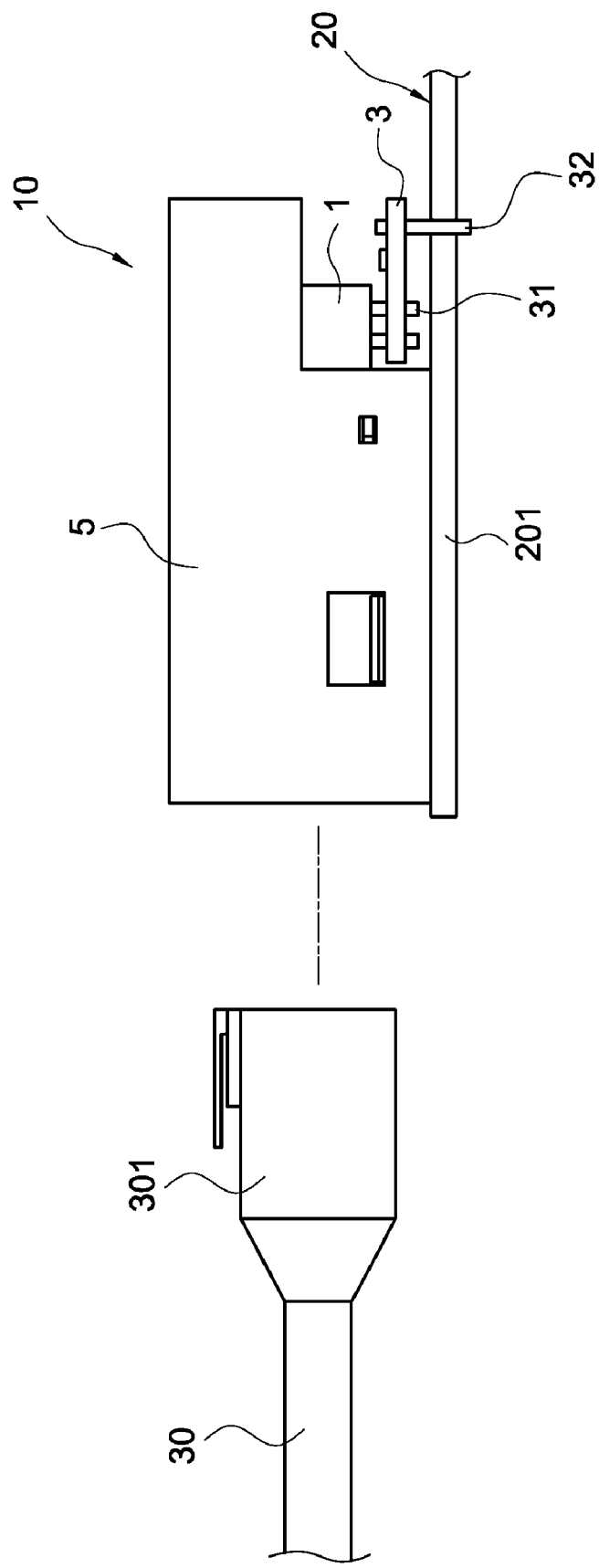
FIG. 3 is a schematic view showing a first operating state of the network socket connector of the present invention.

Please refer to FIG. 3, which is a schematic view showing a first operating state of the network socket connector of the present invention. As shown in this figure, when the network socket connector 10 is electrically connected to the main board 201 of an electronic device 20, a plug 301 of a RJ-45 type network line 30 is inserted into the connecting port 21 of the network socket connector 10. In this way, the network line 30 can be electrically connected with the electrode terminals 14 so as to access the Internet. Then, the tuner of the network AV streaming broadcast circuit 33 on the circuit board 3 receives and switches the channel signals of wireless television net and cable television net. Further, the user can transmit personal AV signals to others by means of the tuner.

Figure 4:
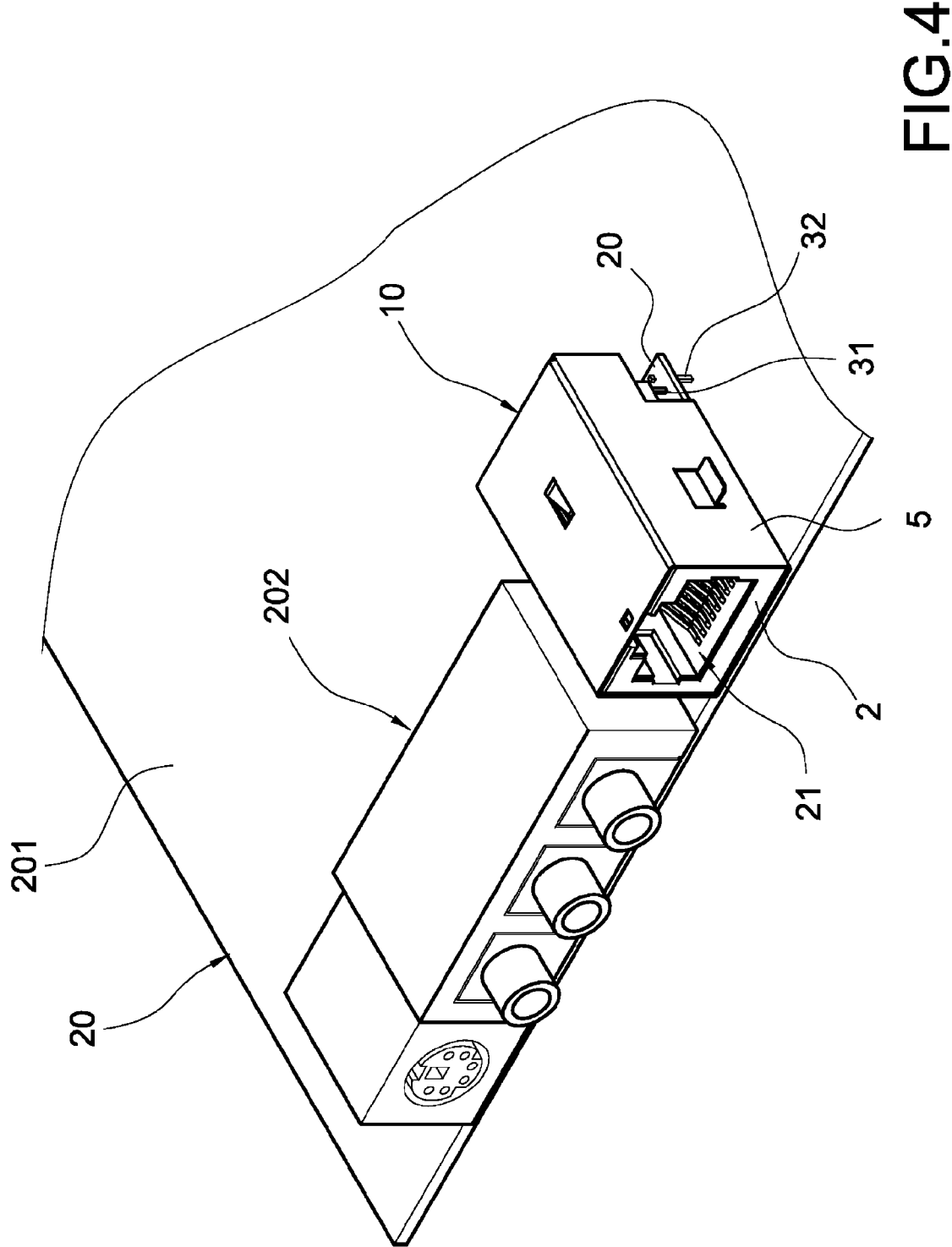
FIG. 4 is a schematic view showing a second operating state of the network socket connector of the present invention.

Please refer to FIG. 4, which is a schematic view showing a second operating state of the network socket connector of the present invention. As shown in this figure, when the network socket connector 10 is electrically connected with the circuit board 201 of the electronic device 20, the main board 201 has signal input ports for various standards of AV terminals 202. The AV terminals 202 are connected to various AV output apparatuses (such as conventional analog or digital cameras, recorders, DVD players or the like). When the plug 301 of the network line 30 is inserted into the network socket connector to access the Internet by means of the network AV streaming broadcast circuit, another function of receiving remote control can be achieved.

Although the present invention has been described with reference to the foregoing preferred embodiments, it will be understood that the invention is not limited to the details thereof. Various equivalent variations and modifications can still occur to those skilled in this art in view of the teachings of the present invention. Thus, all such variations and equivalent modifications are also embraced within the scope of the invention as defined in the appended claims.

What is claimed is:

1. A network socket connector with built-in IP BOX function, electrically connected with a main board of an electronic device and inserted by a plug of a network line, the network socket connector including:
   a base with its rear surface having a plurality of conductive pins extending outside the base and its front surface having a plurality of electrode terminals, the plurality of electrode terminals being electrically connected to the plurality of conductive pins by means of electronic components;
   a front cover assembled at a front end of the base, the front cover having a connecting port, the interior of the connecting port having a plurality of insertion slots for the insertion of the plurality of electrode terminals; and
   a circuit board with its one end having a plurality of insertion holes for the insertion of the conductive pins to be electrically connected to the circuit board, a plurality of conductive terminals being provided on the circuit board adjacent to the insertion holes to be electrically connected to the main board, the circuit board having a network AV streaming broadcast circuit.

2. The network socket connector with built-in IP BOX function according to claim 1, wherein the base is configured as a hollow casing.

3. The network socket connector with built-in IP BOX function according to claim 2, wherein the electronic components are constituted of a first adapting circuit board, a second adapting circuit board and a filter module, the filter module is disposed inside the base, the first adapting circuit board is disposed above the substrate, the second adapting circuit board is disposed in front of the base, the filter module is electrically connected to the first adapting circuit board disposed above the base and the second adapting circuit board disposed in front of the base, the first adapting circuit board is electrically connected to the conductive pins extending outside the base, and the second adapting circuit board is electrically connected with the electrode terminals.

4. The network socket connector with built-in IP BOX function according to claim 1, wherein the network AV streaming broadcast circuit is integrated therein with image, sounds and various network communication protocols, the network AV streaming broadcast circuit has a tuner for receiving and switching channel signals of wireless television net, and cable television net and for transmitting AV signals to the Internet.

5. The network socket connector with built-in IP BOX function according to claim 4, wherein the network socket connector is electrically connected to the main board, the main board has signal input ports for various standards of AV terminals, the AV terminals are connected to various AV output apparatuses, and another function of receiving remote control is achieved when the plug of the network line is inserted into the network socket connector to access the Internet by means of the network AV streaming broadcast circuit.

6. The network socket connector with built-in IP BOX function according to claim 5, wherein the AV output apparatus comprises any one of analog or digital cameras, recorders, and DVD players.

7. The network socket connector with built-in IP BOX function according to claim 1, further including an upper cover assembled to the base and the front cover.

8. The network socket connector with built-in IP BOX function according to claim 7, further including a metallic housing configured to be a hollow body for sealing the base, the front cover, the circuit board and the upper cover.

* * * * *